(12) United States Patent
Ashwood et al.

(10) Patent No.: US 7,262,169 B1
(45) Date of Patent: Aug. 28, 2007

(54) PROCESS FOR PREPARING PEPTIDE INTERMEDIATES

(75) Inventors: Michael Stewart Ashwood, Bishops Stortford (GB); Brian Christopher Bishop, Harlow (GB); Ian Frank Cottrell, Hertford (GB); Khateeta Moneek Emerson, London (GB); David Hands, London (GB); Guo Jie Ho, Quincy, MA (US); Joseph Edward Lynch, Plainfield, NJ (US); Yao Jun Shi, Edison, NJ (US); Robert Darrin Wilson, London (GB)

(73) Assignees: Merck & Co., Inc., Rahway, NJ (US); Merck Sharp & Dohme Limited, Hoddesdon, Hertfordshire (GB)

( * ) Notice: Subject to any disclaimer, the term of this patent is extended or adjusted under 35 U.S.C. 154(b) by 1032 days.

(21) Appl. No.: 10/111,154

(22) PCT Filed: Oct. 18, 2000

(86) PCT No.: PCT/GB00/04019

§ 371 (c)(1),
(2), (4) Date: Aug. 5, 2002

(87) PCT Pub. No.: WO01/29065

PCT Pub. Date: Apr. 26, 2001

(30) Foreign Application Priority Data

Oct. 19, 1999 (GB) ................................ 9924759.5

(51) Int. Cl.
 *A61K 31/00* (2006.01)
(52) U.S. Cl. ....................... 514/16; 530/333; 530/329
(58) Field of Classification Search .................... None
 See application file for complete search history.

(56) References Cited

U.S. PATENT DOCUMENTS

| 4,376,765 A | 3/1983 | Trouet et al. |
| 4,703,107 A | 10/1987 | Monsigny et al. |
| 5,962,216 A | 10/1999 | Trouet et al. |

FOREIGN PATENT DOCUMENTS

| WO | WO 96/00503 | | 1/1996 |
| WO | WO 98/10651 | | 3/1998 |
| WO | WO 98/18493 | | 5/1998 |
| WO | WO 99/02175 | | 1/1999 |
| WO | WO 99/28345 | | 6/1999 |
| WO | WO99/44628 | * | 9/1999 |
| WO | WO 99/44628 | | 9/1999 |
| WO | WO 01/28593 | * | 4/2001 |

OTHER PUBLICATIONS

J. of Med. Chem. vol. 26, No. 5 (1983), pp. 638-644, by P. K. Chakravarty, et al.
Tetrahedron Letter, vol. 40 (1999), pp. 2045-2048, by J. Klose, et al.
Principals of Piptide Synthesis—2nd Edition XP-002162628 (1993), pp. 29-38 & 75-79, by M. Bodansky.
J. Org. Chem, vol. 60 (1995), pp. 3569-3570, by Guo-Jie Ho, et al.
Tetrahedron Letter, vol. 55 (1999), pp. 6813-6830, by L. A. Carpino, et al.
Int. J. Peptide Protein Res., vol. 21 (1983), pp. 196-201, by M. A. Bednarek, et al.
Protein Conjugates with Vinca Alkaloids and Chemotherapy (1985), pp. 323-324 , by K. S. P. Bhushana Rao, et al.
The Cancer Journal from Scientific American, vol. 4, Supp. 1 (1998), pp. S15-S21, by S. R. Denmeade, et al.
Cancer Research, vol. 58 (1998), pp. 2537-2540, by S. R. Denmeade, et al.
Cancer Research, vol. 57 (1997), pp. 4924-4930, by S. R. Denmeade, et al.
Anticancer Research, vol. 9 (1989), pp. 619-624, by K. S. P. Bhushana Rao, et al.
Anticancer Research, vol. 9 (1989), pp. 973-980, by K. S. P. Bhushana Rao, et al.
Anticancer Research, vol. 9 (1989), pp. 625-630, by M. Collard, et al.

* cited by examiner

*Primary Examiner*—B. Dell Chism
*Assistant Examiner*—Hemant Khanna
(74) *Attorney, Agent, or Firm*—David A. Muthard; Mark R. Daniel

(57) ABSTRACT

The present invention is directed to the improved synthesis of compounds of formula (I) an intermediate compound which is useful in the synthesis of the anticancer agents known as PSA conjugates.

26 Claims, No Drawings

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Completely synthetic amino acid sequence
<220> FEATURE:
<221> NAME/KEY: VARIANT
<222> LOCATION: (1)...(1)
<223> OTHER INFORMATION: Xaa=cyclohexylglycine
<220> FEATURE:
<221> NAME/KEY: VARIANT
<222> LOCATION: (4)...(4)
<223> OTHER INFORMATION: Xaa=leucine benzyl ester

<400> SEQUENCE: 1

Xaa Gln Ser Xaa
 1

<210> SEQ ID NO 2
<211> LENGTH: 4
<212> TYPE: PRT
<213> ORGANISM: Artificial Sequence
<220> FEATURE:
<223> OTHER INFORMATION: Completely synthetic amino acid sequence
<220> FEATURE:
<221> NAME/KEY: VARIANT
<222> LOCATION: (1)...(1)
<223> OTHER INFORMATION: Xaa=cyclohexylglycine
<220> FEATURE:
<221> NAME/KEY: VARIANT
<222> LOCATION: (4)...(4)
<223> OTHER INFORMATION: Xaa=O-protected leucine

<400> SEQUENCE: 2

Xaa Gln Ser Xaa
 1

<210> SEQ ID NO 3
<211> LENGTH: 7
<212> TYPE: PRT
<213> ORGANISM: Artificial Sequence
<220> FEATURE:
<223> OTHER INFORMATION: Completely synthetic amino acid sequence
<220> FEATURE:
<221> NAME/KEY: VARIANT
```

```
<222> LOCATION: (1)...(1)
<223> OTHER INFORMATION: Xaa=N-(fluorenylmethoxyglutaryl)-trans-4-
      hydroxy-L-proline
<220> FEATURE:
<221> NAME/KEY: VARIANT
<222> LOCATION: (4)...(4)
<223> OTHER INFORMATION: Xaa=cyclohexylglycine
<220> FEATURE:
<221> NAME/KEY: VARIANT
<222> LOCATION: (7)...(7)
<223> OTHER INFORMATION: Xaa=O-protected-leucine

<400> SEQUENCE: 3

Xaa Ala Ser Xaa Gln Ser Xaa
 1               5

<210> SEQ ID NO 4
<211> LENGTH: 4
<212> TYPE: PRT
<213> ORGANISM: Artificial Sequence
<220> FEATURE:
<223> OTHER INFORMATION: Completely synthetic amino acid sequence
<220> FEATURE:
<221> NAME/KEY: VARIANT
<222> LOCATION: (1)...(1)
<223> OTHER INFORMATION: Xaa=N-benzyloxycarbonyl-cyclohexylglycine
<220> FEATURE:
<221> NAME/KEY: VARIANT
<222> LOCATION: (4)...(4)
<223> OTHER INFORMATION: Xaa=leucine benzyl ester

<400> SEQUENCE: 4

Xaa Gln Ser Xaa
 1

<210> SEQ ID NO 5
<211> LENGTH: 7
<212> TYPE: PRT
<213> ORGANISM: Artificial Sequence
<220> FEATURE:
<223> OTHER INFORMATION: Completely synthetic amino acid sequence
<220> FEATURE:
<221> NAME/KEY: VARIANT
<222> LOCATION: (1)...(1)
<223> OTHER INFORMATION: Xaa=N-(fluorenylmethoxyglutaryl)-trans-4-
      hydroxy-L-proline
<220> FEATURE:
<221> NAME/KEY: VARIANT
<222> LOCATION: (4)...(4)
<223> OTHER INFORMATION: Xaa=cyclohexylglycine

<400> SEQUENCE: 5

Xaa Ala Ser Xaa Gln Ser Leu
 1               5

<210> SEQ ID NO 6
<211> LENGTH: 7
<212> TYPE: PRT
<213> ORGANISM: Artificial Sequence
<220> FEATURE:
<223> OTHER INFORMATION: Completely synthetic amino acid sequence
<220> FEATURE:
<221> NAME/KEY: VARIANT
<222> LOCATION: (1)...(1)
<223> OTHER INFORMATION: Xaa=N-(fluorenylmethoxyglutaryl)-trans-4-
      hydroxy-L-proline
<220> FEATURE:
<221> NAME/KEY: VARIANT
<222> LOCATION: (4)...(4)
<223> OTHER INFORMATION: Xaa=cyclohexylglycine
<220> FEATURE:
<221> NAME/KEY: VARIANT
<222> LOCATION: (7)...(7)
```

```
<223> OTHER INFORMATION: Xaa=leucine benzyl ester

<400> SEQUENCE: 6

Xaa Ala Ser Xaa Gln Ser Xaa
 1               5
```

PROCESS FOR PREPARING PEPTIDE INTERMEDIATES

PRIORITY CLAIM

This application is a §371 application of PCT/EP00/04019 that was filed on Oct. 18, 2000, which claims priority from the Great Britain Application No. GB 9924759.5, filed on Oct. 19, 1999, now expired.

BACKGROUND OF THE INVENTION

Compositions useful in the treatment of prostatic cancer and related conditions are described in U.S. Pat. Nos. 5,599,686 and 5,866,679; and U.S. patent application Ser. No. 08/950,805, filed 14 Oct. 1997 (corresponding to International Patent Publication No. WO 98/18493) entitled Conjugates Useful in the Treatment of Prostate Cancer. Said compositions, which may be termed PSA conjugates, comprise chemical conjugates comprising known cytotoxic agents and oligopeptides having amino acid sequences that are selectively proteolytically cleaved by free prostate specific antigen and, with respect to Ser. No. 08/950,805 (corresponding to U.S. Pat. No. 5,948,750, issued on 7 Sep. 1999), that include a cyclic amino acid having a hydrophilic substituent. The oligopeptide moieties are selected from oligomers that are selectively recognised by free prostate specific antigen (PSA) and are capable of being proteolytically cleaved by the enzymatic activity thereof.

Ideally, the cytotoxic activity of the cytotoxic agent is greatly reduced or absent when the intact oligopeptide containing the PSA proteolytic cleavage site is bonded directly, or through a chemical linker, to the cytotoxic agent. Also ideally, the cytotoxic activity of the cytotoxic agent increases significantly, or is restored completely, upon proteolytic cleavage of the attached oligopeptide at the cleavage site. Preferably, the N-terminus of the oligopeptide is protected by a hydrophilic blocking group, of which glutaric acid and succinic acid are preferred examples. Such protected oligopeptides may be illustrated by the following structure:

Protecting group—$AA_1$-$AA_2$-$AA_3$-$AA_4$-$AA_5$-$AA_6$-$AA_7$ wherein $AA_1$, $AA_2$, $AA_3$, $AA_4$, $AA_5$, $AA_6$ and $AA_7$ are independently selected from a natural and unnatural amino acid. It is understood that protected oligopeptides having greater or fewer amino acid residues (from 5 to 10 amino acids) may alternatively be incorporated in the PSA conjugate.

Among the preferred N-terminus protecting groups that are incorporated onto a PSA conjugate are the dicarboxylic acid alkanes, such as succinyl, glutaryl and the like. Therefore a preferred protected oligopeptide may be illustrated by the formula:

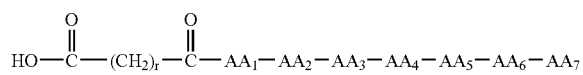

To ensure selective attachment of the cytotoxic agent via the $AA_7$ residue, the free carboxylic acid group of the protecting group must be blocked. A suitable blocking group for this purpose is the 9-fluorenylmethyl ester (Fm), since it is readily removed under mild conditions (20% piperidine) at the end of the process. Thus, key intermediates in the synthesis of the desired PSA conjugates are compounds of formula A:

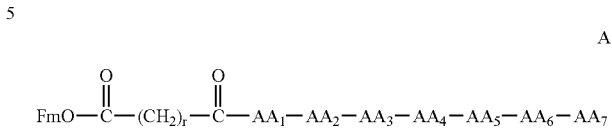

In several of the specific examples disclosed in WO 98/18493, the conjugate comprises an oligopeptide having the amino acid sequence:

and the cytotoxic agent is attached to the C-terminus (i.e. via the carboxyl group of the $AA_7$ residue). Thus, in a preferred preparative process, the desired cytotoxic agent is attached to the $AA_7$ residue of a peptide analogue of Formula B:

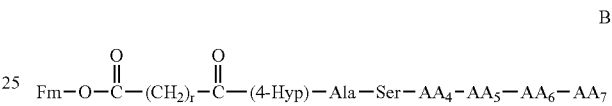

where Fm represents 9-fluorenylmethyl and r is 2 or 3.

As disclosed in the above-referenced patent application, such compounds may be prepared by a linear strategy involving conventional techniques of solid-phase peptide synthesis. However, such methods are best suited to laboratory-scale synthesis, rather than factory-scale preparations. Furthermore, the solid-phase process requires the use of anhydrous HF, which necessitates special handling techniques and precautions.

An alternative strategy, more amenable to scale-up, involves the preparation of a tripeptide analogue of Formula (C):

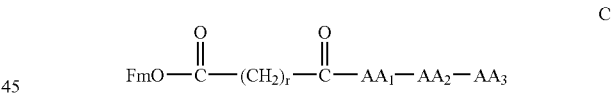

and in particular the intermediate compound of the Formula (C-1)

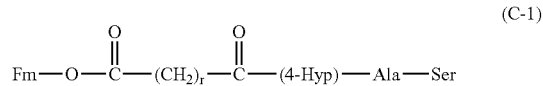

where Fm and r are as previously defined, followed by coupling of the protected tripeptide (C) to the appropriate tetrapeptide.

Compounds of Formula (C-1) therefore represent important synthetic targets. Although a conventional solution-phase strategy, starting with serine, may be employed for the synthesis of such compounds, the results are disappointing. In particular, it is necessary to protect both the hydroxyl group and the carboxylic acid group of serine (e.g. as the benzyl ether and p-nitrobenzyl ester, respectively) during the assembly of the peptide chain and the introduction of the Fm-blocked glutaryl or succinyl group. Attempts to remove these protecting groups invariably lead to partial cleavage of the Fm blocking group, with consequent reductions in yield and/or purity of the desired products.

Thus, there is a continuing need for a convenient, clean, high-yield process for the synthesis of peptidyl intermediate compounds useful in the synthesis of PSA conjugates, in particular the intermediate compounds of Formula (C) and the precursor compounds of the Formula (A), suitable for use on an industrial scale.

SUMMARY OF THE INVENTION

The instant invention provides a process for preparing intermediate compounds of the Formula B which utilizes solution phase chemistry.

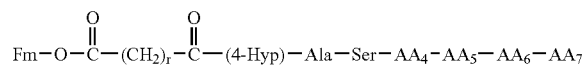

B

The instant process comprises the step of reacting the diester of the formula E:

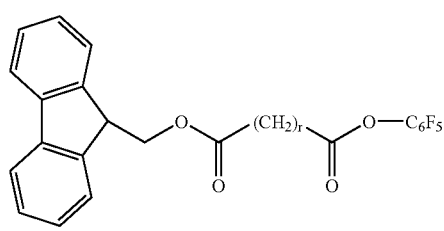

E with the tripeptide D:

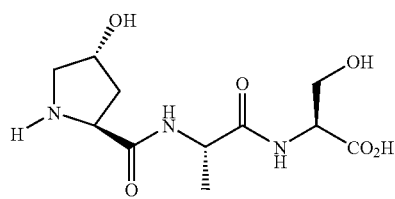

D or a salt thereof;
to provide an intermediate of the formula C-1:

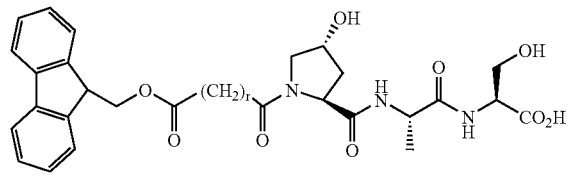

C-1 or a salt thereof.

DETAILED DESCRIPTION OF THE INVENTION

The instant invention provides a process for preparing intermediate compounds of the Formula B which utilizes solution phase chemistry.

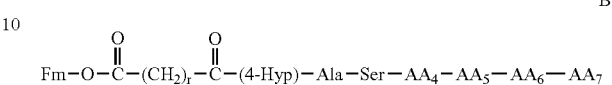

B

The instant process comprises the step of reacting the diester of the formula E:

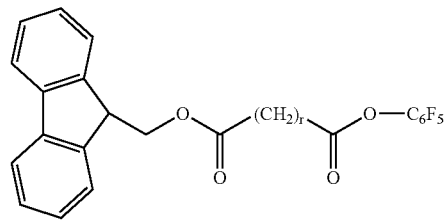

E with the tripeptide D:

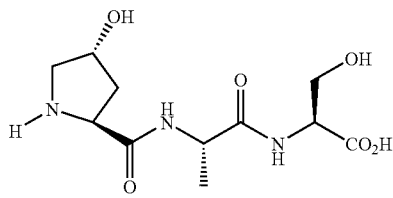

D or a salt thereof;
to provide an intermediate of the formula C-1:

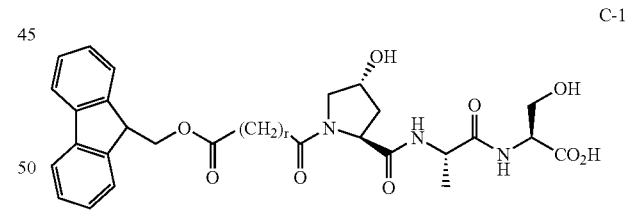

C-1 or a salt thereof.

The invention further provides a process for preparing an intermediate compound of Formula C-1:

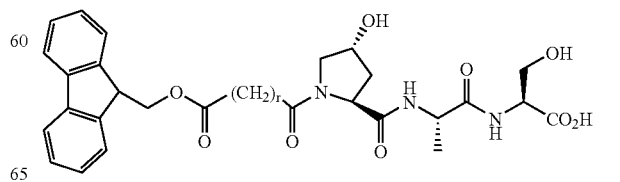

C-1 where r is 2 or 3, which comprises in sequence, the steps of:
(i) reacting unprotected alanine-serine with the pentafluorophenyl ester of N-protected 4-hydroxyproline to form N-protected 4-hydroxyproline-alanine-serine;
(ii) removing the N-protection from the product of step (i); and
(iii) reacting the product of step (ii) with a compound of Formula E

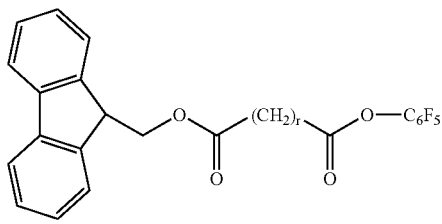

where r is 2 or 3.

The process of the invention provides a convenient and efficient route to the preparation of N-terminus-protected oligopeptides that are useful as intermediates in the preparation of PSA conjugates. In comparison with the alternatives available, the inventive process involves fewer steps, and provides products of higher purity in greater yields. Readily available starting materials are used, and all steps in the process are suitable for factory-scale operations.

The instant invention also provides compounds that are particularly useful as intermediates in the syntheses of the oligopeptide intermediates. Among those intermediate compounds are the compound of the formula C-1:

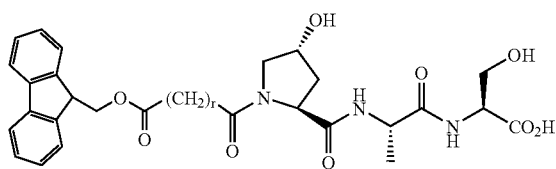

and the compound H-Chg-Gln-Ser-Leu-O-benzyl (SEQ. ID. NO.: 1)

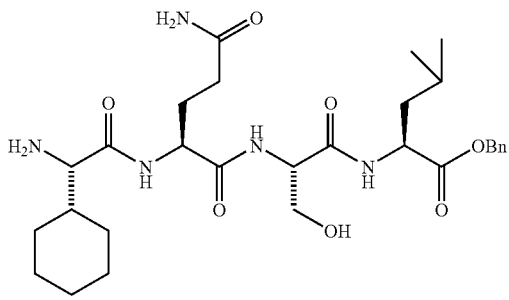

or a salt thereof.

A key feature of the process is the formation of amide bonds by reaction of the appropriate amine components with pentafluorophenyl esters of the appropriate acid components. The relevant pentafluorophenyl esters are stable crystalline solids, readily prepared in bulk for storage prior to use. The pentafluorophenyl esters react smoothly with the amine components under mild conditions to produce the desired amides in high yields. The desired amides are readily separable from the by-product, pentafluorophenol, which may be recovered in high yield and recycled. Furthermore, free hydroxyl groups and carboxylic acid groups are unaffected by the reaction conditions, and hence do not require protection. This simplifies the process greatly in comparison to alternative methodologies.

As used herein, the term natural amino acid represents those amino acids that are coded by the codons of mRNA.

As used herein, the term unnatural amino acid represents those amino acids that are not coded by the codons of mRNA, Preferably, unnatural amino acids are α amino acids.

The starting materials for the inventive process are commercially available, or readily synthesized, amino acids, dipeptides, tripeptides and tetrapeptides. In a preferred embodiment, the starting material is the dipeptide alanine-serine:

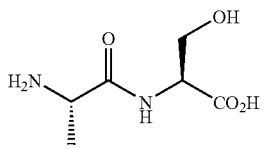

which is available commercially in bulk from suppliers such as Bachem AG, Hauptstrasse 144, CH-4416, Bubendorf, Switzerland.

In the first step of the process, the amino group of the dipeptide is reacted with the pentafluorophenyl ester of N-protected 4-hydroxyproline, forming the N-protected tripeptide 4-Hyp-Ala-Ser:

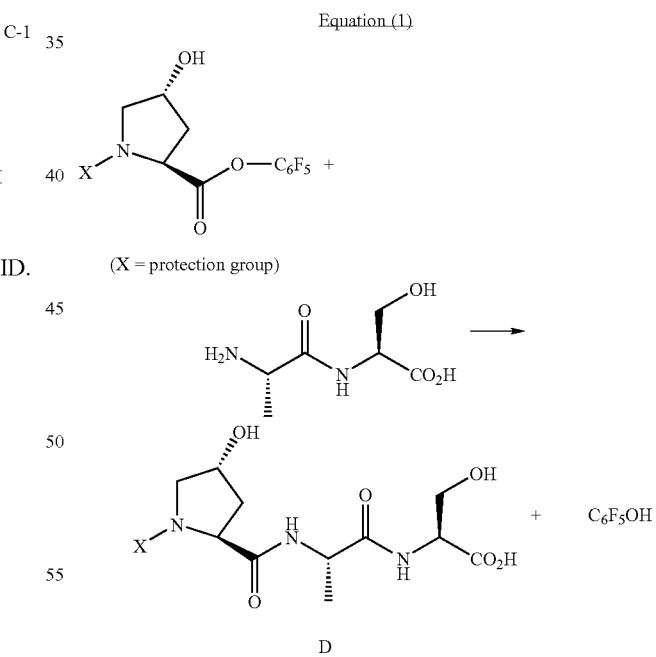

Equation (1)

(X = protection group)

Protection of the amino functionality of 4-hydroxyproline is necessary in order to prevent self-condensation. Such use of amino-protecting groups is routine in peptide synthesis, and one skilled in the art is referred to texts such as *Protective Groups in Organic Chemistry*, McOmie, ed., Plenum Press, NY (1973); and *Protective Groups in Organic Synthesis*, Green ed., John Wiley & Sons, NY (1981) for examples of protective groups which may be useful in this context.

While it is not necessary in the synthesis of the preferred intermediate compound D as shown above, one of ordinary skill in the art would appreciate that the carboxylic acid (carboxy) moiety of the readily available dipeptide, and additionally or alternatively the hydroxy moiety(ies) of the hydroxyproline and the dipeptide, may optionally be protected prior to the tripeptide forming reaction, and then subsequently deprotected.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

A preferred amino-protecting group is t-butoxycarbonyl (Boc), formed by reaction of the amine with di-tert-butyl-dicarbonate under alkaline conditions, and cleavable by acid hydrolysis.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl)silyl, such as trimethylsilyl, β-p-toluenesulfonylethyl, β-p-nitrophenylthio-ethyl, 2,4,6-trimethylbenzyl, β-methylthioethyl, phthalimidomethyl, 2,4-dinitro-phenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

The salts of the compounds useful in the processes of this invention include the conventional salts of basic compounds from inorganic or organic acids or salts of acidic compounds from inorganic or organic bases. For example, such conventional salts of basic compounds include (but are not limited to) those derived from inorganic acids such as hydrochloric, hydrobromic, sulfuric and the like, and the salts prepared from organic acids such as toluenesulfonic, methanesulfonic, trifluoromethanesulfonic, ethane disulfonic, trifluoroacetic and the like. Examples of conventional salts of acidic compounds include (but are not limited to) those derived from inorganic bases such as sodium, potassium, cesium, lithium, ammonium, calcium and the like, and the salts prepared from organic bases such as triethylammonium, ethyldiisopropylammonium, benzyl amine, bicyclohexylamine (BCHA) and the like.

The pentafluorophenyl ester of N-protected 4-hydroxyproline may be prepared by reaction of the N-protected amino acid with pentafluorophenol using any of the standard techniques for ester formation. In a preferred method, the amino acid is reacted with a slight excess of pentafluorophenol in the presence of excess dicyclohexylcarbodiimide in acetonitrile solution or ethyl acetate.

Formation of the tripeptide, as depicted in Equation (1), requires only mild heating (e.g. to about 50° C.) for a short time (about 2–about 3 hours) in an inert solvent such as dimethylformamide (DMF).

The next step in the inventive process is removal of the N-protecting group from the tripeptide. In the case of the preferred Boc protecting group, this is most conveniently achieved by acid treatment of the crude product obtained from the first step. In a typical process, the solvent is evaporated under reduced pressure, and the residue is stirred at room temperature for 24 hours with a mixture of concentrated hydrochloric acid and isopropanol. After further dilution with isopropanol, the pure tripeptide is obtained (as its hydrochloride salt) as a crystalline solid in high yield.

The next step in the process of the invention is the attachment of the 9-fluorenylmethyl succinate or glutarate residue to the N-terminus of the tripeptide. This is achieved by reaction of the tripeptide (as the free amine) with a succinate or glutarate mixed diester of Formula (E):

(E)

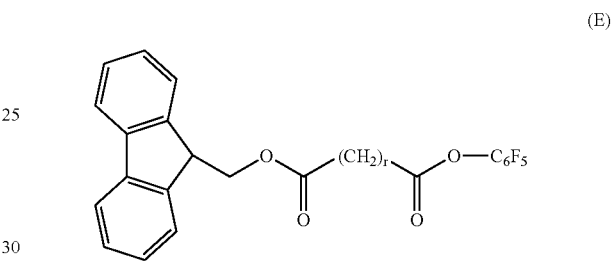

(r=2 or 3)

as depicted in Equation (2):

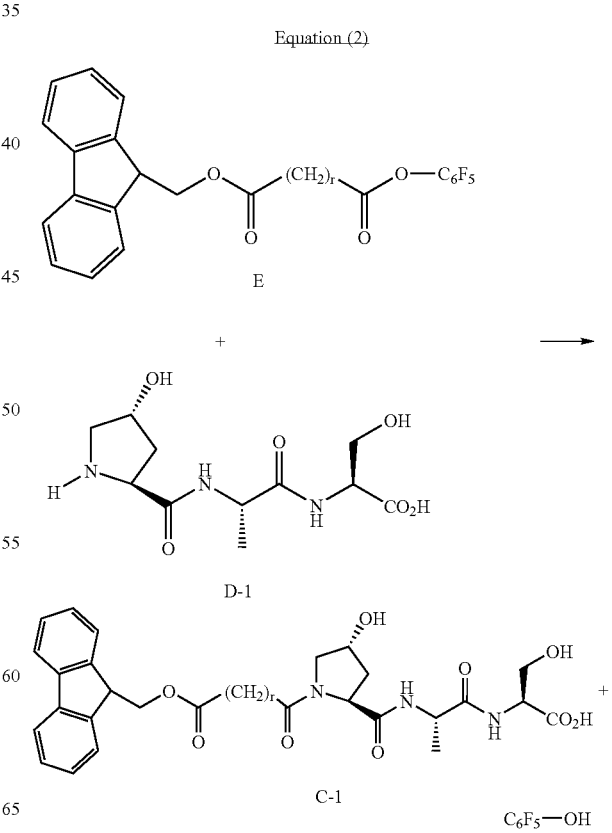

The mixed diesters (E) are readily prepared in two stages from succinic anhydride (r=2) or glutaric anhydride (r=3). In the first stage, the appropriate cyclic anhydride is reacted with 0.5 equivalents of 9-fluorenyl methanol to form the fluorenylmethyl mono-ester of succinic or glutaric acid. In the second stage, reaction of the mono-ester with pentafluorophenol under standard esterification conditions affords the mixed diester.

The coupling reaction depicted in Equation (2) takes place under similar conditions to those described above for the analogous reaction depicted in Equation (1). However, if the tripeptide is initially present as the hydrochloride (or other salt), one molar equivalent of a base, such as a tertiary amine or the like, must first be added to the reaction mixture to liberate the free amine.

The intermediate compound C-1 may be readily isolated and purified by evaporating the solvent and partitioning the residue between water and a suitable organic solvent, such as tert-butyl methyl ether. Work-up of the aqueous phase affords the crude product, which may be purified by crystallisation, typically in two steps, firstly from isopropanol, and secondly from 5:1 v/v mixture of ethyl acetate and methanol.

The N-protected tripeptide intermediate may then be coupled to a second polypeptide intermediate (F) which is separately prepared by standard solution-phase chemistry, to provide the N-protected oligopeptide intermediate (B).

wherein Prot is a carboxylic acid protecting group as described hereinabove.

For the purpose of the peptide coupling reaction, a carboxyl activating agent is usually employed in the presence of a base and optionally in the presence of an additive. The carboxyl activating agent may be selected from the group including, but not limited to, 2-(1H-benzotriazol-1-yl)-1,3,3-tetramethyluronium hexafluorophosphate (known as HBTU), 1-hydroxybenzotriazole hydrate (known as HOBT), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluorophosphate (BOP), 1,3-diisopropylcarbodiimide (DIC) and the like, used in combination or singularly. Preferably the carboxyl activating agent is selected from EDC, DIC and DCC. Most preferably the carboxyl activating agent is EDC.

The peptide coupling reaction may also comprise a base, such as collidine, lutidine, pyridine, triethyl amine, Hünig's base ((iPr)$_2$NEt), N-ethylmorpholine and the like. Preferably the base is selected from collidine, N-ethylmorpholine and lutidine. Most preferably the base is N-ethylmorpholine. The peptide coupling reaction may also comprise an additive, such as 1-hydroxy-7-azabenzotriazole (HOAt), 1-hydroxybenzotriazole (HOBt), N-hydroxysuccinimide, pyridine N-oxide, 4-hydroxypyridine N-oxide and the like. Preferably the additive is selected from HOAt, 4-hydroxypyridine

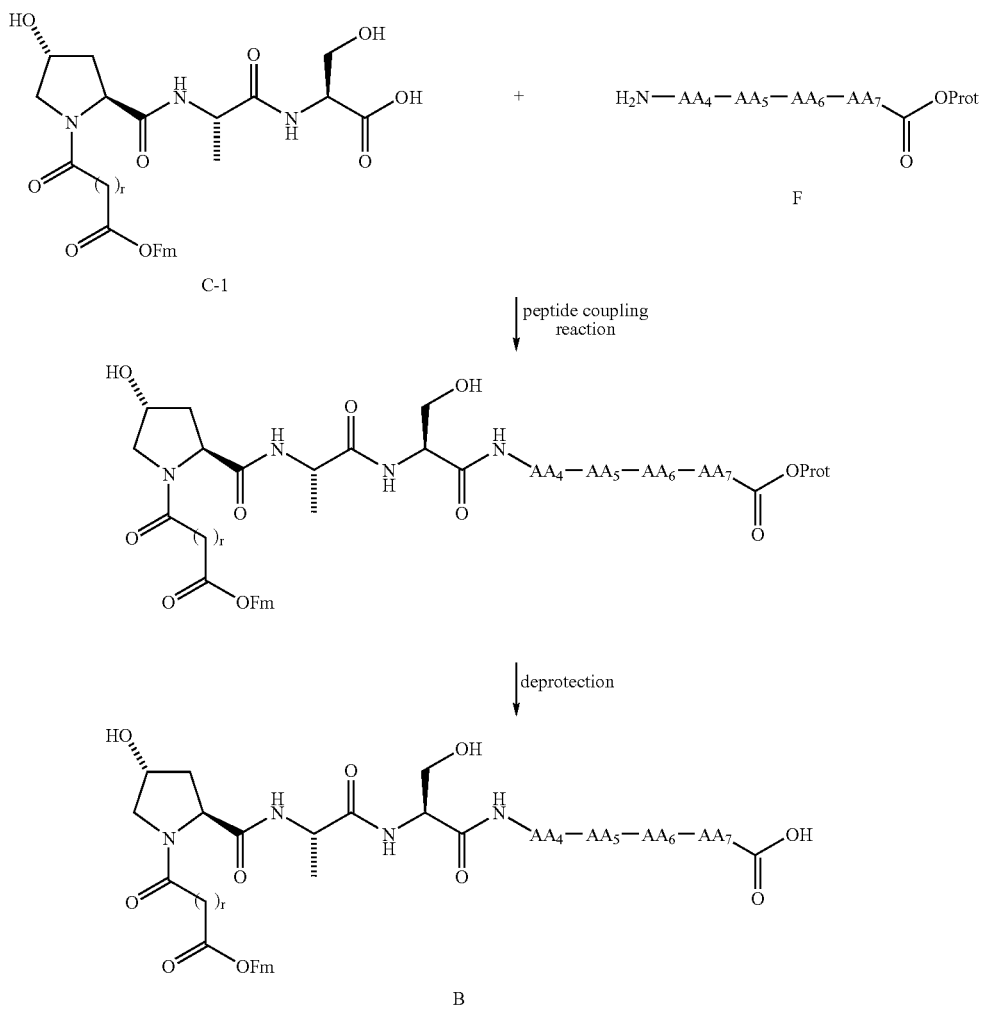

N-oxide and HOBt. Most preferably the additive is 4-hydroxypyridine N-oxide. The peptide coupling reaction may also comprise a solvent. Such a solvent may be selected from N,N-dimethylformamide (DMF), N,N-dimethylacetamide (DMAc), N-methylpiperidone (NMP), aqueous THF, and the like. Preferably the solvent is selected from a polar aprotic organic solvent, such as DMF, DMAc, NMP and the like. Most preferably, the solvent is DMF.

Preferably, Prot is a benzyl group, which may be removed by catalytic hydrogenation, such as treatment with $H_2$ over Pd/C or the like (H. Paulsen. And M. Schultz, *Liebigs Ann. Chem.* 1986:1435–1447; R. C. Kelly et al., *J. Org. Chem.* 51:4590–4594 (1986)). Preferably, removal of the benzyl group by hydrogenation is carried out in the absence of acid. However, hydrogenation may be effected in the additional presence of an organic acid, such as methane sulfonic acid, toluenesulfonic acid and the like. Where acid is added to the hydrogenation reaction, preferably the acid is methane sulfonic acid.

A specific example of the instant process in one in which the C-terminus protected tetrapeptide of the formula F is C-terminus protected Chg-Gln-Ser-Leu, wherein Chg is cyclohexylglycine. This specific synthesis is illustrated in the following scheme:

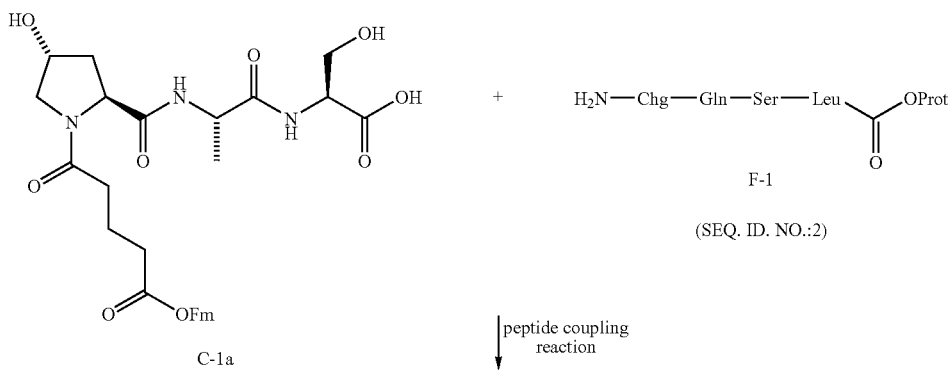

C-1a

F-1

(SEQ. ID. NO.:2)

peptide coupling reaction

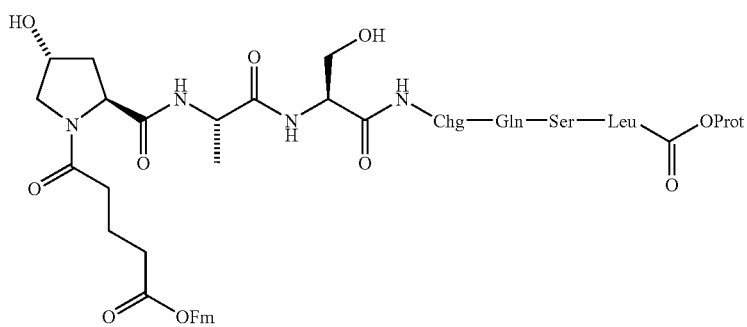

(SEQ. ID. NO.:3)

deprotection

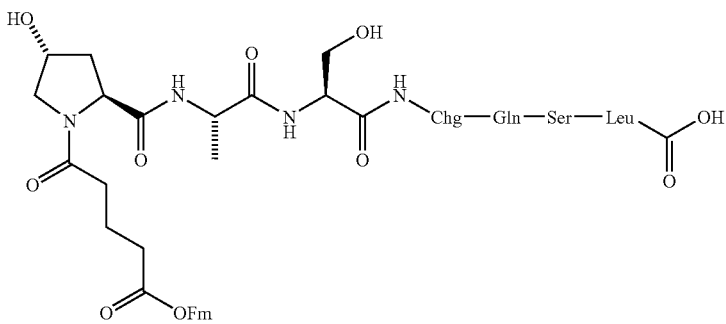

(SEQ. ID. NO.:5)

B-1

Preferably, with respect to the synthesis of the compound of formula B-1, the crude product of the deprotection reaction illustrated above is purified by slurrying the crude product in a polar solvent, such as methanol, ethanol and the like, and then adding an anti-solvent, such as ethyl acetate, isopropyl acetate and the like, and then collecting the purified compound B-1. Preferably, this slurrying purification procedure (which can also be termed a "swish purification") is performed twice on the crude product from the deprotection.

Intermediate (B) may then be coupled to a cytotoxic agent (such as doxorubicin, as shown in the scheme below) to provide the desired PSA conjugate, as illustrated in the following scheme:

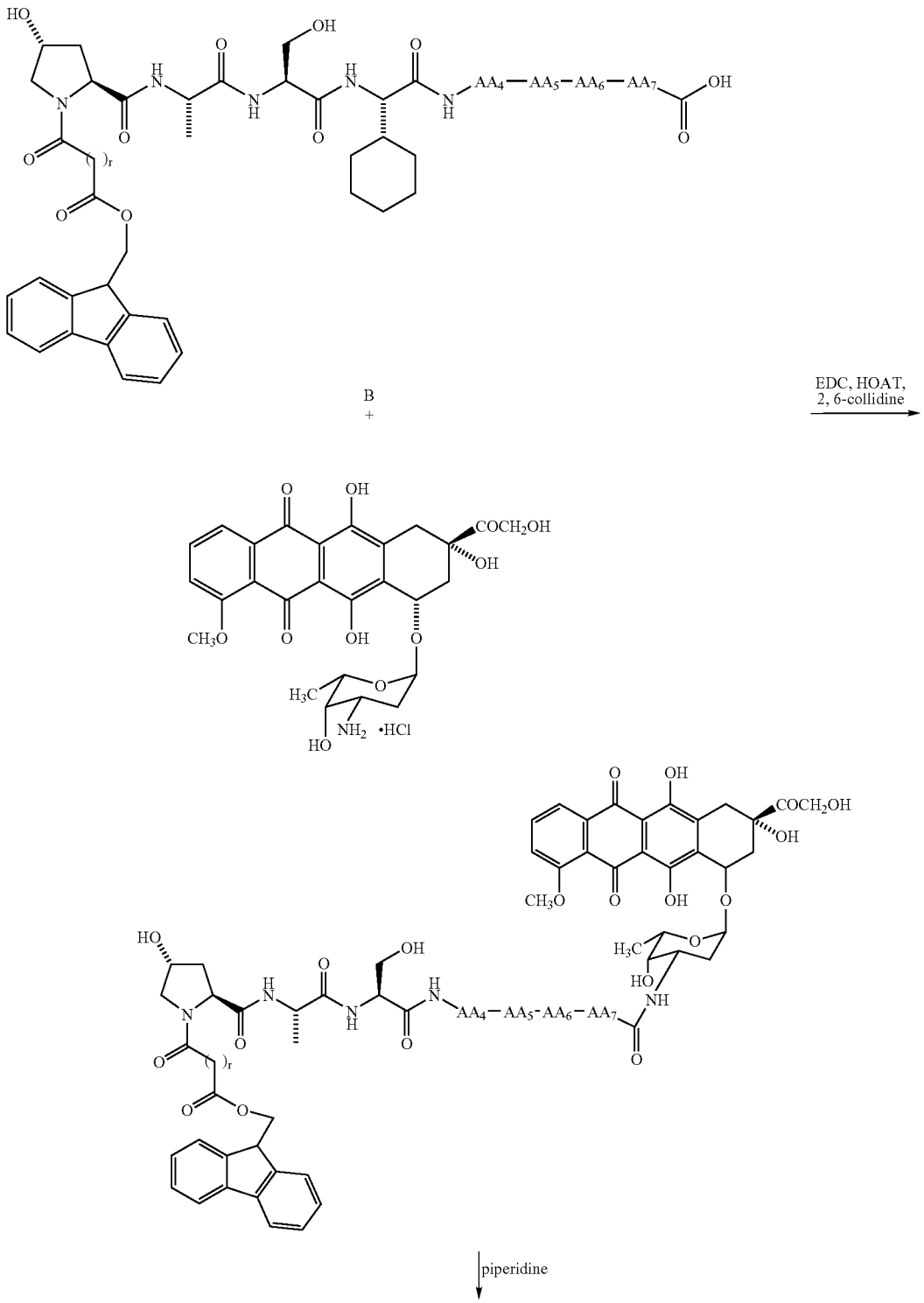

-continued

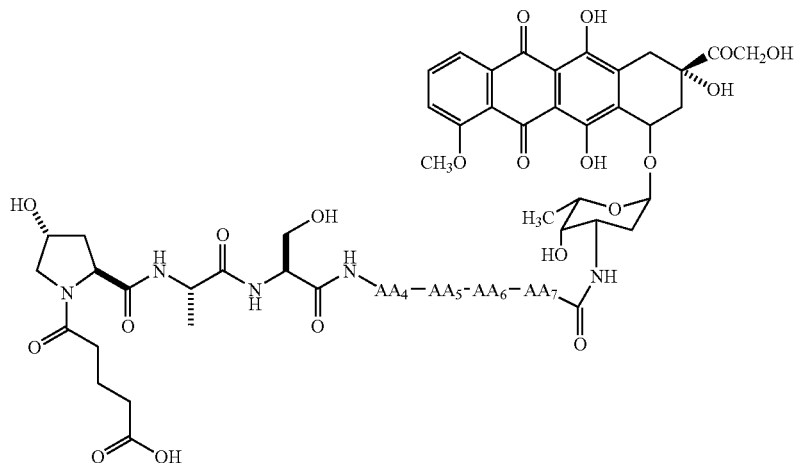

The following non-limiting Examples illustrate the process of the present invention:

EXAMPLE 1

Experimental Procedure for the Preparation of Fm-glutaryl-Hyp-Ala-Ser-OH

Step 1: Boc-Trans-4-Hydroxy-L-Proline

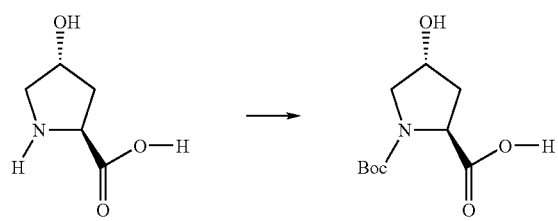

A solution of trans-4-hydroxy-L-proline (3.0 kg, 22.88 M) in 1 M aqueous sodium hydroxide (25.2 L) and tert-butanol (12.0 L) was treated with a solution of di-tert-butyldicarbonate (5.09 kg) in tert-butanol (6.0 L) at 20° C. over 20 minutes. Upon complete addition, the resulting solution was stirred at 20° C. for 2 hours. The solution was extracted with hexane (2×15.0 L) and then acidified to pH 1 to 1.5 by cautious addition of a solution of potassium hydrogen sulphate (3.6 kg) in water (15.0 L). The mixture was extracted with ethyl acetate (3×15.0 L). The combined ethyl acetate extracts were washed with water (2×1.0 L) and dried by azeotropic distillation at atmospheric pressure.

The ethyl acetate solution was then concentrated by atmospheric distillation to a volume of 15.0 L, diluted with hexane (8.0 L), seeded and stirred at 20° C. for 1 hour. Hexane (22.5 L) was added over 2 hours, the slurry was cooled to 0° C. for 1 hour and the solid collected by filtration. The product was washed with cold (0° C.) 2:1 hexane/ethyl acetate (15.0 L) and dried in vacuo at 45° C. to afford the title compound as a white crystalline solid. Yield; 4.306 kg, 81%. HPLC; >99 A %.

Step 2: Boc-Trans-4-Hydroxy-L-Proline Pentafluorophenyl Ester

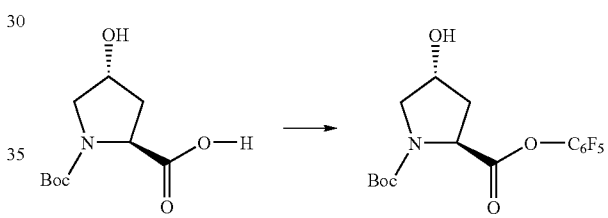

Boc-trans-4-hydroxy-L-proline (3.5 kg) and pentafluorophenol (3.06 kg) were dissolved in ethyl acetate (52 L). The solution was treated with a solution of dicyclohexylcarbodiimide (3.43 kg) in ethyl acetate (8 L) and the mixture was stirred at room temperature for 2 hours. The resulting slurry was cooled to 0° C., filtered and the solids washed with ethyl acetate (15 L). The filtrate was evaporated at atmospheric pressure to a volume of 10 L and diluted with hexane (100 L). The resulting mixture was stirred at room temperature overnight and then cooled to 0° C. for 1 hour. The solid was collected by filtration, washed with cold (° C.) 10:1 hexane/ethyl acetate (15 L) and dried at 45° C. in vacuo to afford the title compound as a white crystalline solid. Yield: 5.478 kg, 91%. HPLC; >99 A %.

Step 3: Fluorenylmethyl Glutarate

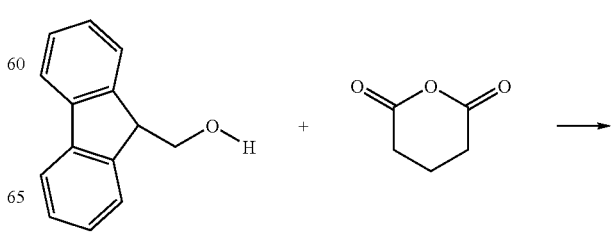

-continued

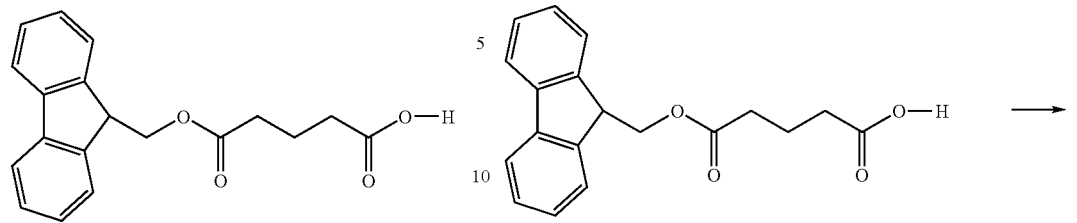

Step 4: Fluorenylmethyl Glutarate Pentafluorophenyl Ester

9-Fluorenyl methanol (2.0 kg), glutaric anhydride (2.33 kg) and sodium bicarbonate (1.71 kg) were stirred together in N-methylpyrrolidinone (8.0 L) at room temperature for 72 hours. The slurry was filtered and the solids washed with isopropyl acetate (2×10.0 L). The filtrate was washed with 1.0 M hydrochloric acid (3×10.0 L). The organic layer was extracted with 1.0 M aqueous sodium hydroxide (3×8.0 L). The combined basic extracts were covered with isopropyl acetate (20.0 L) and acidified to pH 2 with 2.0 M hydrochloric acid (12.5 L). The phases were separated and the aqueous phase was extracted with isopropyl acetate (10.0 L).

The combined organic phases were washed with water (10.0 L) and dried by azeotropic distillation at <60° C. under reduced pressure (KF<0.05%). The solution was then concentrated under reduced pressure (<60° C.) to a volume of 7.0 L. The solution was diluted with hexane (6.0 L), seeded and stirred at room temperature for 30 minutes. The resulting slurry was diluted by addition of hexane (42.0 L) over 40 minutes. The slurry was cooled to 0° C. for 1 hour and the solid collected by filtration and washed with cold (0° C.) 8:1 hexane/isopropyl acetate (20.0 L). The solid was dried in vacuo at 45° C. to afford the title compound as a pale cream solid. Yield: 2.676 kg, 85%. HPLC; >99 A %.

Fluorenylmethyl glutarate (2.5 kg) and pentafluorophenol (1.63 kg) were dissolved in ethyl acetate (25 L). The solution was treated with a solution of dicyclohexylcarbodiimide (1.83 kg) in ethyl acetate (7.5 L) and the mixture was stirred at 20° C. overnight. The resulting slurry was filtered and the solids were washed through with ethyl acetate (10 L). The filtrate was evaporated at atmospheric pressure to a volume of 7.5 L and diluted with hexane (75 L). The slurry was filtered at 60–65° C. then allowed to cool to room temperature and stirred overnight. The slurry was cooled to 0° C. for 1 hour, the solid collected by filtration and washed with 10:1 hexane/ethyl acetate (15 L). The solid was dried in vacuo at 45° C. to afford the title compound as a white crystalline solid. Yield: 3.553 kg, 93%. HPLC; >99 A %.

Step 5: HCl.Hyp-Ala-Ser-OH

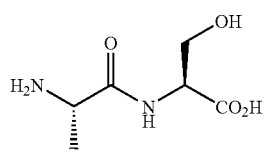

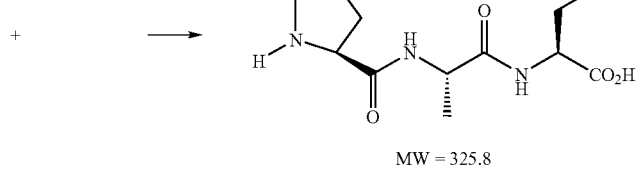

MW = 325.8

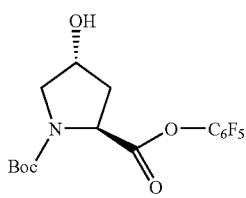

Ala-Ser-OH (1.5 kg, 8.515 M) and Boc-trans-4-hydroxy-L-proline (3.72 kg) were heated at 50° C. in dimethylformamide (15 L) for 3 hours. The solution was cooled to 20° C., treated with concentrated hydrochloric acid (7.5 L) and stirred at room temperature for 24 hours. The resulting slurry was diluted with isopropanol (30 L), stirred at room temperature for 30 minutes and then cooled to 0° C. for 1 hour. The solid was collected by filtration and washed with isopropanol (20 L). The solid was dried in vacuo at 40° C. to afford the title compound as a white crystalline solid. Yield: 2.505 kg, 90%. HPLC; >99 A %.

Step 6: Fm-glutaryl-Hyp-Ala-Ser-OH

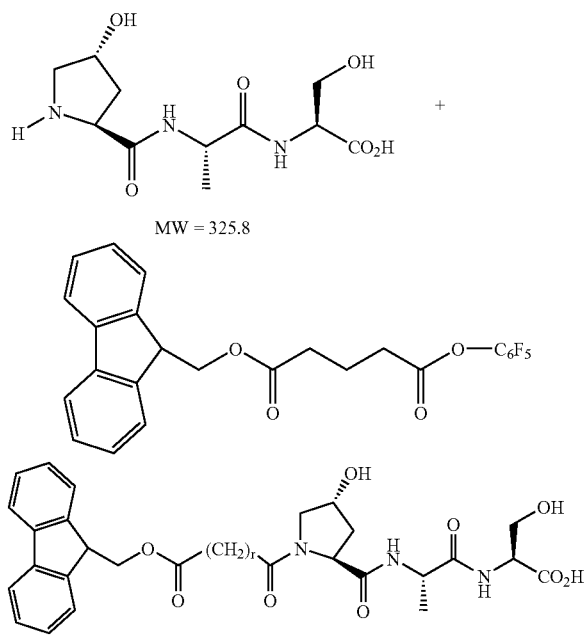

HCl.Hyp-Ala-Ser-OH (2.3 kg) was suspended in dimethylformamide (22 L) and the slurry was treated with N-ethylmorpholine (911 ml) followed by a solution of fluorenylmethyl glutarate pentafluorophenyl ester (3.5 kg) in dimethylformamide (14 L). The mixture was heated at 50° C. for 3 hours and the resulting solution evaporated to residue under reduced pressure. The residue was partitioned between water (80 L) and tert-butyl methyl ether (34 L). The phases were separated and the aqueous layer was extracted with tert-butyl methyl ether (34 L). The aqueous solution was seeded and stirred at room temperature overnight. The solid was collected by filtration (slow) and washed with water (25 L). The damp filter cake was dissolved in isopropanol (90 L) with warming and the solution concentrated to half volume by distillation at atmospheric pressure. Additional portions of isopropanol (3×45 L) were added and the batch was concentrated to ca half volume by atmospheric distillation after addition of each portion. The slurry was diluted with isopropanol (23 L), stirred at 20° C. overnight, cooled to 0° C. for 1 hour and the solid collected by filtration. The cake was washed with isopropanol (20 L) and the solid dried in vacuo at 45° C. to afford the crude product as a white solid. Yield: 3.447 kg, 84%. HPLC 99.0 A %.

Step 7: Recrystallisation of Fm-Glutaryl-Hyp-Ala-Ser-OH

Fm-Glutaryl-Hyp-Ala-Ser-OH (3.4 kg) was dissolved in methanol (51 L) at reflux. The solution was filtered and concentrated by atmospheric distillation to a volume of 17 L (5 ml/g). The solution was diluted with ethyl acetate (102 L) allowed to cool to 20° C. and stirred overnight. The resulting slurry was cooled to 0° C. for 1 hour and the solid was collected by filtration. The cake was washed with cold (0° C.) 10:1 ethyl acetate/methanol (20 L) and dried in vacuo at 45° C. to afford the product as a white solid. Recovery: 3.349 kg, 98.5%, HPLC; 99.3 A %.

$^{13}$C NMR (100.62 MHz, DMSO-$d_6$, 50° C.):

Chemical shifts in ppm referenced to solvent DMSO central line at 39.9 ppm. 173.5, 173.0, 172.6, 172.3, 171.8, (C=O); 144.6, 141.7, 128.6, 128.0, 125.9, 121.0, (Aromatic C and CH); 69.6, 59.3, 55.5, 49.0, 47.3, (CH); 66.2, 59.4, 56.0, 38.7, 33.7*, 20.65, (CH$_2$); 18.5, (CH$_3$).

*Two different carbons at same chemical shift.

EXAMPLE 2

Experimental Procedure for the Preparation of HCl.H-Chg-Gln-Ser-Leu-O-benzyl

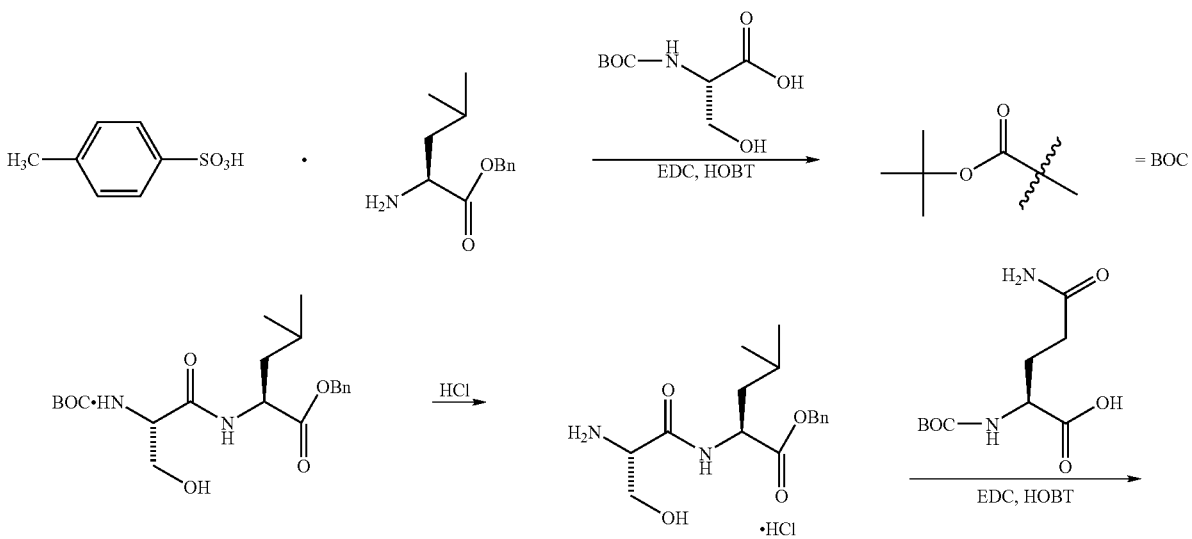

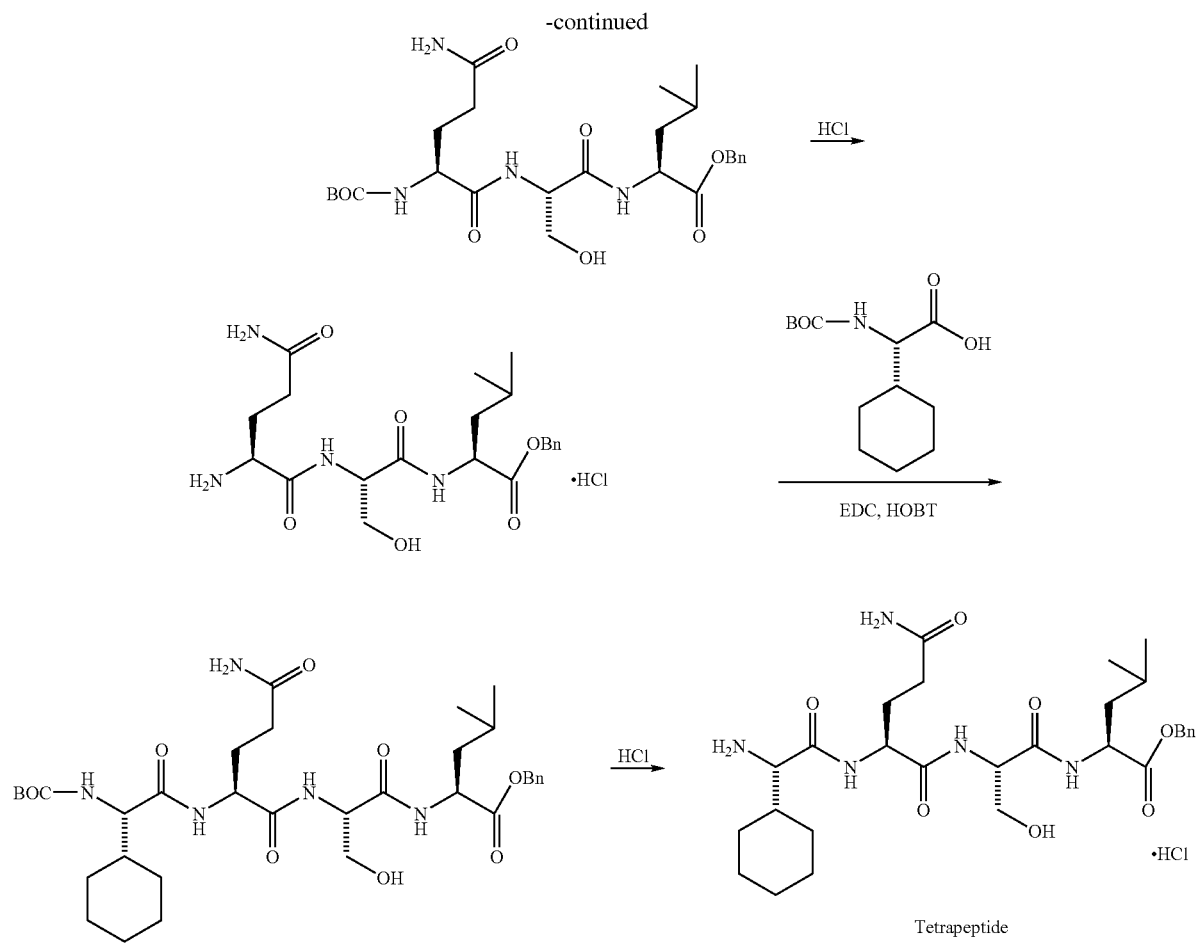

Step 1: HCl.H-Ser-Leu-O-benzyl

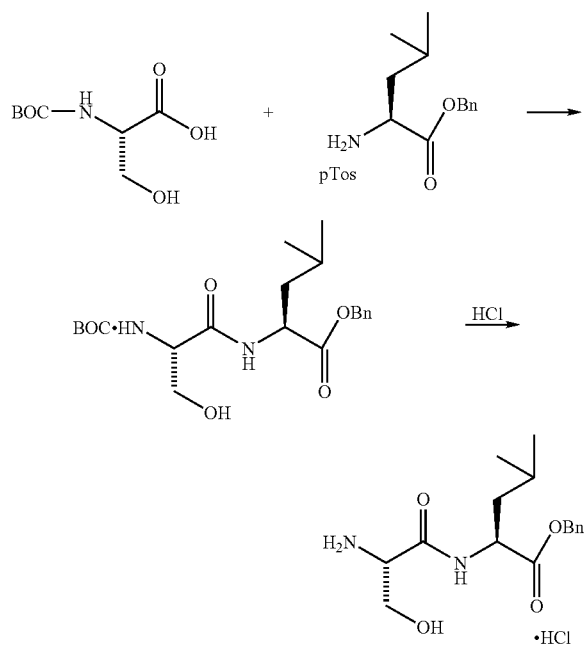

Leucine benzyl ester p-tosylate (1000 g) and HOBt (412 g) were slurried in isopropyl acetate (12 L). The mixture was cooled to 0° C. in an ice-bath and a slurry of sodium bicarbonate (469.7 g) in water (1 L), N—BOC-L-serine (573.6 g) in water (2 L) and EDC.HCl (560.2 g) in water (2 L) were added. The mixture was allowed to warm to 20° C. over 30 minutes and aged at 20° C. for 2 hours. If the reaction was not complete after 2 hours, further NaHCO$_3$ and EDC.HCl were added. The phases were separated and the organic layer was washed sequentially with saturated sodium bicarbonate (2×3.75 L), 0.5 M sodium hydrogen sulphate (2×3.75 L) and water (2×2.5 L).

The wet, isopropyl acetate solution was concentrated under reduced pressure to 3 L and the water content checked. (KF=0.12%. It is important that this solution is dry prior to the addition of hydrogen chloride in isopropyl acetate). The solution was transferred to a 20 L round bottom flask under a nitrogen atmosphere and cooled to 0° C. To the solution was added 3.6 M HCl in isopropyl acetate (7 L, 10 mol equiv. HCl). The product began to crystallise after 5 minutes. The reaction was aged at 0° C. for 1 hr, and then allowed to warm to room temperature.

The slurry was cooled to 0–5° C., diluted with heptane (2.5 L) and aged at 0° C. for 30 minutes. The product was collected by filtration, washed with cold isopropyl acetate/ heptane (4:1) (2.5 L) and dried in vacuo at 35° C., with a nitrogen sweep. Yield=824.6 g, 94%; LCAP>99.5 A % at 210 nm, (melting point=158–160° C.).

Step 2: N-Boc-Gln-Ser-Leu-O-benzyl

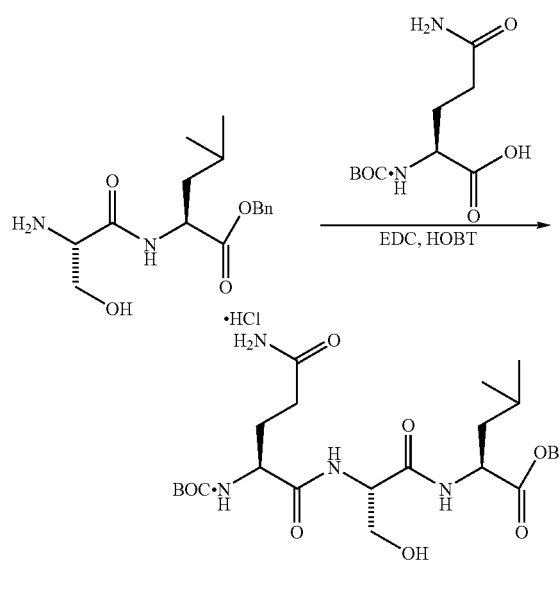

HCl.H-Ser-Leu-OBn (350 g), HOBt (157.7 g) and N-Boc-L-glutamine (262.5 g) were slurried in DMF (2.5 L) and the mixture was cooled to 0° C. N-Ethylmorpholine (245.5 g) and EDC.HCl (214 g) were added and the mixture was aged at 0° C. for 2.5 hours. Water (14.7 L) was added over 20 minutes and the white slurry aged at 0° C. for 1 hour. The product collected by filtration and washed with water (3.2 L). The cake was dried in the fume-hood overnight. The isolated N—BOC-Gln-Ser-Leu-OBn, which contained DMF and HOBt, was combined with a second batch of identical size, and swished in water (12 L) at 20° C. for 1 hour. The product was collected by filtration, washed with water (2.5 L) and air-dried in a fume-hood over the weekend. The batch was dried in vacuo, at 42° C., with a nitrogen bleed. Yield for the combined batches=1037.4 g, 93.8%, HPLC>98.7 A %, (melting point=145–147° C.).

Step 3: HCl.H-Gln-Ser-Leu-O-benzyl

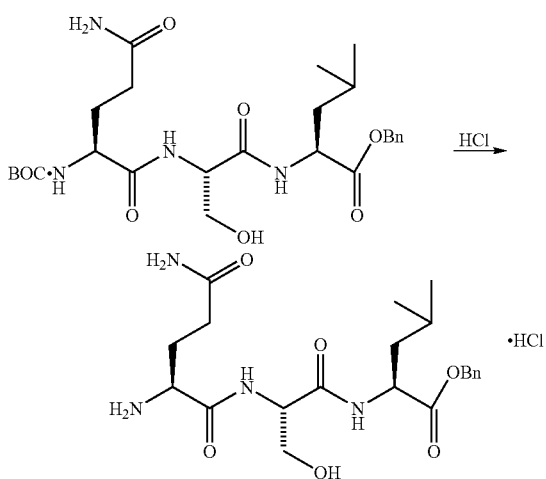

Boc-Gln-Ser-Leu-OBn (715 g, 1.33 M) was suspended in isopropyl acetate (3.5 L) at room temperature. To the slurry was added a 3.8 M solution of HCl in isopropyl acetate (3.5 L, 13.3 M) whereupon all the solids dissolved. After a short time, the product crystallised. The mixture was stirred at room temperature for 3.75 hours when HPLC showed complete reaction. The slurry was diluted with isopropyl acetate (4.0 L), stirred for 1 hour at room temperature and the solid collected by filtration under nitrogen. The product is very hygroscopic in the presence of excess HCl and must be collected under dry nitrogen.

The cake was washed with isopropyl acetate (4.0 L), the solid dried on the filter under nitrogen for 2 hours and then dried in vacuo at 45° C. Yield; 622.8 g, 99%. HPLC; 96.4 A %.

Step 4: Boc-Chg-Gln-Ser-Leu-O-benzyl (SEQ. ID. NO.: 4)

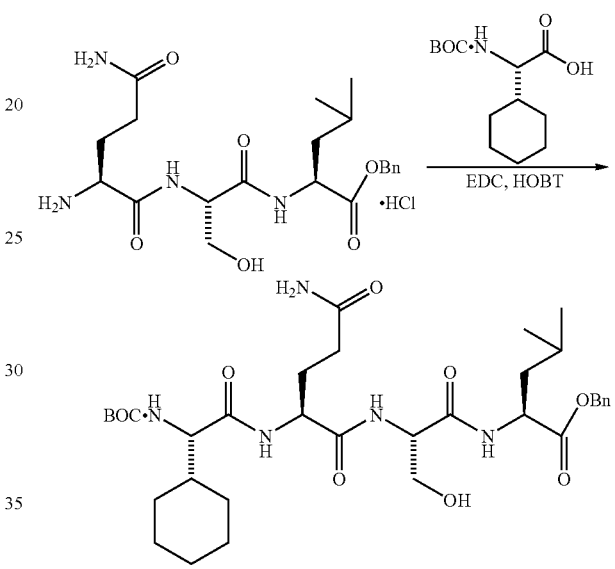

HCl.H-Gln-Ser-Leu-OBn (2.6 kg), Boc-L-cyclohexylglycine (1.414 kg) and HOBt hydrate (168 g) were dissolved in DMF (13.0 L). N-ethylmorpholine (1.266 kg, 11.0 M) and EDC hydrochloride (1.265 kg) were added and the mixture stirred at 20° C. for 3 hours. The solution was diluted with ethyl acetate (13.0 L) and water (26.0 L) added. The product precipitated and the slurry was stirred at room temperature for 1 hour. The solid was collected by filtration, washed with 1:1 ethyl acetate/water (60 L) dried on the filter under nitrogen for 24 hours and dried in vacuo at 45° C. The title compound was obtained as a white solid. Yield: 3.449 kg, 93%. HPLC; 96.0 A %.

Step 5: HCl.H-Chg-Gln-Ser-Leu-O-benzyl (SEQ. ID. NO.: 1)

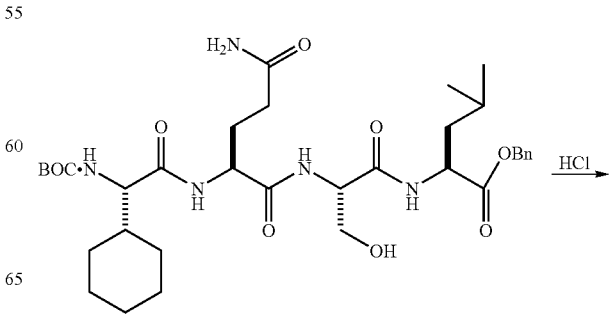

-continued

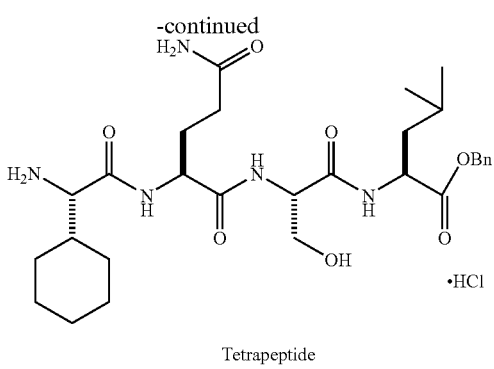

Tetrapeptide

N-Boc-Chg-Gln-Ser-Leu-OBn (1850 g) was slurried in isopropyl acetate (3.2 L). The slurry was cooled to 0° C. in an ice bath and 3.8 M HCl/isopropyl acetate (3.7 L, 11.4 mol equiv.) was added over 5 minutes, maintaining the temperature between 8 and 10° C. The starting material had dissolved after 15–20 minutes. The solution was seeded and the reaction aged at 8–10° C. for 2 hrs, (<1 A % N-Boc-tetrapeptide-OBn remaining). The batch was filtered, under a nitrogen blanket, washed with cold (10° C.) isopropyl acetate (4×3 L) then dried on the filter under nitrogen. The solid was dried in vacuo, at 40° C. Yield=795.9 g (76% wt % assay, 83.5 A %).

Step 6: Swish Procedure

The crude HCl. Chg-Gln-Ser-Leu (2.2 Kg) was slurried in methanol (22.3 L) at room temperature. The batch was stirred for 1 hour and then ethyl acetate (44.6 L) was added over 30 minutes. The batch was cooled to 0–5° C., aged for one hour, then filtered and washed with cold (0–5° C.) methanol/ethyl acetate (6 L, 1:2). The solid was dried on the filter, under nitrogen, for 45 minutes and then dried in vacuo, at 40° C., with a nitrogen sweep. HCl.tetrapeptide (1.478 Kg, 95.7 A % (210 nm), 90.4% w/w) was obtained in 83.1% recovery from the N-Boc.tetrapeptide-OBn.

The HCl.tetrapeptide (1.478 Kg) was slurried in methanol (14.8 L) at room and the batch stirred for 1 hr. Ethyl acetate (29.6 L) was added over 30 minutes, the batch was cooled to 0–5° C. and aged for an hour. The solid collected by filtration, washed with cold (0–5° C.) methanol/ethyl acetate (4.5 L, 1:2), dried on the filter for 45 minutes, under nitrogen, and then dried under vacuum, at 40° C. HCl.tetrapeptide (1.343 Kg, 97.5 A % (210 nm), 96.3% w/w, mp: 254–256° C.) was obtained in 61% yield from the N-Boc. tetrapeptide-OBn.

$^{13}$C NMR (100.62 MHz, DMSO-$d_6$, 50° C.):

Chemical shifts in ppm referenced to solvent DMSO central line at 39.5 ppm. 174.9, 172.9, 171.5, 170.8, 168.6, (C=O); 136.8, 129.3, 128.9, 128.6, (Aromatic C and CH); 57.8, 56.1, 53.3, 51.5, 39.9, 29.2, (CH); 66.8, 62.5, 32.4, 29.0, 28.8, 26.4, 26.3, 25.1, (CH$_2$); 23.5, 22.4, (CH$_3$).

EXAMPLE 3

Fm-Glutaryl-Hyp-Ala-Ser-Chg-Gln-Ser-Leu-OH (SEQ. ID. NO.: 5)

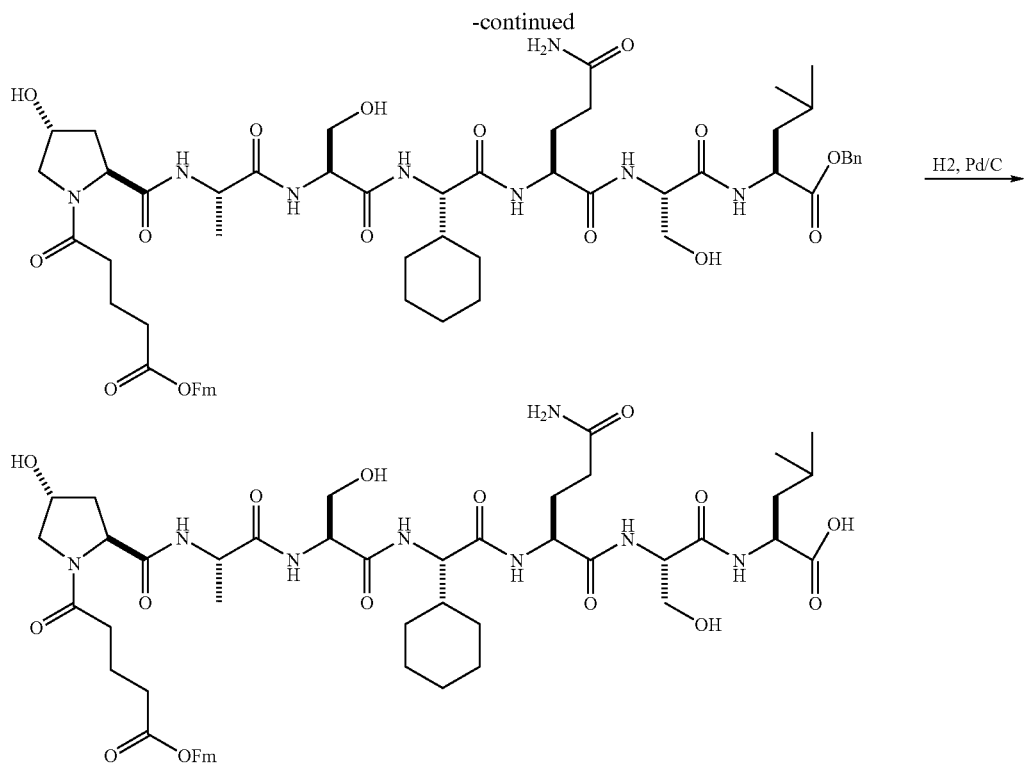

Step 1: Fm-Glutaryl-Hyp-Ala-Ser-Chg-Gln-Ser-Leu-O-benzyl (SEQ. ID. NO.: 6)

HCl.H-Chg-Gln-Ser-Leu-OBn (500 g), Fm-Glutaryl-Hyp-Ala-Ser-OH (490 g) and HOAt (160 g) were slurried in DMF (8.2 L) and cooled to 2° C. in an ice bath. N-ethylmorpholine (135 ml) was added followed by EDC.HCl (210 g). The mixture was stirred at 0–2° C. for 2 hours and sampled. HPLC showed 0.2 A % tetrapeptide remaining. The reaction mixture was diluted with ethyl acetate (4 L) and transferred to a 30-gallon glass vessel through a 5µ in-line filter. The flask and lines were rinsed with ethyl acetate/DMF (1:1, 500 ml) and ethyl acetate (4 L). Water (16.4 L) was added over 25 minutes (temperature 11° C. to 23° C.) and the mixture stirred slowly, at 20° C., for 30 minutes. The product was collected by filtration, washed with water (3 L), ethyl acetate (1 L) and water (2×3 L), then dried on the filter under nitrogen, and dried in vacuo at 45° C. Yield=900 g, 97.0% yield. HPLC 96.5 A %.

Alternative Step 1: Fm-Glutaryl-Hyp-Ala-Ser-Chg-Gln-Ser-Leu-O-benzyl (SEQ. ID. NO.: 6)

HCl.H-Chg-Gln-Ser-Leu-OBn (100 g), Fm-Glutaryl-Hyp-Ala-Ser-OH (98 g) and 4-hydroxypyridine-N-oxide (HOPO, 18.2 g) were slurried in DMF (1.6 L) and cooled to 2° C. in an ice bath. N-ethylmorpholine (27 ml) was added followed by EDC.HCl (42 g). The mixture was stirred at 2–5° C. for 4 hours and sampled. HPLC showed 0.6 A % tetrapeptide remaining. The reaction mixture was diluted with ethyl acetate (1.64 L), water (3.3 L) was added over 70 minutes and the mixture stirred slowly, at 20° C., for 60 minutes. The product was collected by filtration, washed with water (1.5 L), ethyl acetate (1 L) and water (3×1 L), then dried on the filter under nitrogen, and dried in vacuo at 45° C. Yield=186 g, 100.0% yield. HPLC 98.0 A %.

Step 2: Fm-Glutaryl-Hyp-Ala-Ser-Chg-Gln-Ser-Leu-OH (SEQ. ID. NO. 5)

Fm-Glutaryl-Hyp-Ala-Ser-Chg-Gln-Ser-Leu-OBn (prepared as described in Step 1 or Alternative Step 1) (1.1 Kg) was dissolved in dimethylacetamide (7.8 L) containing methanesulphonic acid (93.5 ml). 5% Pd/C (110 g, 10 wt %), slurried in DMA (1.0 L), was added and the mixture hydrogenated at atmospheric pressure for 1 hour 40 minutes. The reaction mixture was sampled: HPLC showed no starting material remaining.

The reaction mixture was filtered through a pre-wetted (DMA) pad of Hyflo™ (500 g) to remove the catalyst. The hyflo pad washed with DMA (2.2 L) and then ethyl acetate (5.5 L). The filtrate was diluted with ethyl acetate (5.5 L) and stirred for 15 minutes. Water (44 L) was added over 40 minutes and the batch age for 1 hour. The solid collected by filtration, washed with water (1×10 L, 3×20 L), dried on the filter under a nitrogen blanket and dried in vacuo at 45° C. Yield=862.5 g, 85% yield. HPLC 88.3 A %.

Step 3: Fm-Glutaryl-Hyp-Ala-Ser-Chg-Gln-Ser-Leu-OH Swish Purification

Crude Fm-Glutaryl-Hyp-Ala-Ser-Chg-Gln-Ser-Leu-OH (prepared as described in Step 2) (2.58 kg) was sieved in 99% recovery (2.56 Kg). The solid (2.56 Kg) was swished in ethyl acetate for 3 hours. The solid was collected by filtration, washed with ethyl acetate (26 L), dried on the filter under nitrogen and dried in vacuo at 40° C. Yield=2.489 Kg, 96.5% recovery. [95.2 A % by HPLC at 210 nm; KF=0.77 wt %; TGA=1.30 wt %; EtOAc=0.51 wt %]

$^{13}$C NMR (100.62 MHz, DMSO-$d_6$, 70° C.:

Chemical shifts in ppm referenced to solvent DMSO central line at 39.5 ppm. 174.8, 173.3, 172.7, 171.9, 171.5, 171.1, 170.6, (C═O); 144.7, 141.7, 128.5, 127.9, 125.7, 120.8, (Aromatic C and CH); 59.7, 58.7, 56.3, 56.0, 53.7, 51.6, 49.7, 47.6, 40.6, 33.9, (CH); 66.7, 62.2, 40.6, 32.4, 30.0, 28.9, 28.5, 26.6, 26.5, 26.4, 23.4, 22.6, 20.7, (CH$_2$); 23.4, (CH$_3$).

Alternative Hydrogenation Procedure without Added Methanesulphonic Acid

Alternative Step 2: Fm-Glutaryl-Hyp-Ala-Ser-Chg-Gln-Ser-Leu-OH

Fm-Glutaryl-Hyp-Ala-Ser-Chg-Gln-Ser-Leu-OBn (prepared as described in Step 1 or Alternate Step 1) (200 g) was dissolved in dimethylacetamide (1.9 L) at 45–50° C. 5% Pd/C (20 g, 10 wt %) slurried in DMA (100 ml) was added and the slurry was cooled to −5 to −10° C. The mixture was hydrogenated at atmospheric pressure maintaining the temperature between −10 and −5° C. for 5.5 hours. The reaction mixture was sampled and HPLC showed complete reaction.

The mixture was filtered whilst still cold (<0° C.) through a pre-wetted (DMA) pad of Hyflo™ (100 g). The filtrate was diluted with ethyl acetate (2.5 L) and water (8.0 L) was added over 1 hour 15 minutes. The batch was aged for a further 1 hour and the solid was collected by filtration. The cake was washed with water (8.0 L) sucked down on the filter and then dried in vacuo at 45° C. with a nitrogen sweep. Yield=179.9 g, 97.5% yield. HPLC 85.6 A %.

Alternative Step 3: Fm-Glutaryl-Hyp-Ala-Ser-Chg-Gln-Ser-Leu-OH Swish Purification Crude Fm-Glutaryl-Hyp-Ala-Ser-Chg-Gln-Ser-Leu-OH (368.3 g) (prepared as described in Alternative Step 2) was broken up in a mortar and pestle and swished in ethyl acetate (3.5 L) at room temperature for 3 hours. The solid was collected by filtration, washed with ethyl acetate (1.5 L) dried on the filter and dried in vacuo at 45° C. Yield=342.9 g, 93.0% recovery. [94.9 A % by HPLC at 210 nm; KF=2.01 wt %; TGA=5.35 wt %]

What is claimed is:

1. A process for the preparation of a compound of formula B:

$$Fm-O-\overset{O}{\overset{\|}{C}}-(CH_2)_r-\overset{O}{\overset{\|}{C}}-(4-Hyp)-Ala-Ser-AA_4-AA_5-AA_6-AA_7 \quad B$$

or a salt thereof;
wherein
AA$_4$, AA$_5$, AA$_6$ and AA$_7$ are independently selected from a natural or unnatural amino acid;
Fm is 9-fluorenylmethyl;
4-Hyp is

[structure of 4-hydroxyproline residue]

and
r is 2 or 3,
that comprises the steps of:
a) reacting the diester of the formula E:

[structure E: Fm-O-CO-(CH₂)_r-CO-O-C₆F₅]

with the tripeptide D:

[structure D: 4-Hyp-Ala-Ser tripeptide with free CO₂H]

or a salt thereof;

to provide an intermediate of the formula C-1:

[structure C-1]

or a salt thereof;

b) reacting the intermediate of the formula C-1 with a tetrapeptide of the formula F:

$$H_2N-AA_4-AA_5-AA_6-AA_7-C(O)-OProt \quad F$$

wherein Prot is a carboxylic acid protecting group, to provide the following compound of the formula:

[structure with OFm, (CH₂)_r linker, 4-Hyp-Ala-Ser-AA₄-AA₅-AA₆-AA₇-OProt]

and c) deprotecting the C-terminus of the following compound of the formula:

[structure same as above with OFm and OProt]

2. The process according to claim 1 wherein an acid salt of the tripeptide of the formula D is reacted with the diester of the formula E in the presence of a base.

3. The process according to claim 2 wherein the base is a trialkyl amine.

4. The process according to claim 2 wherein the base is triethyl amine.

5. The process according to claim 1 wherein Prot is benzyl.

6. The process according to claim 5 which further comprises the additional step of treating the compound of the formula:

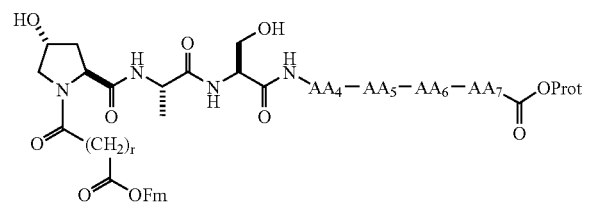

wherein Prot is benzyl, with hydrogen ($H_2$) in the presence of palladium on carbon.

7. The process according to claim 5 which further comprises the additional step of treating the compound of the formula:

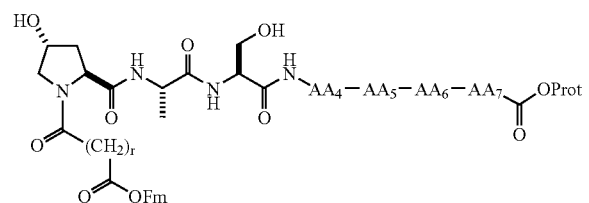

wherein Prot is benzyl, with hydrogen ($H_2$) in the presence of palladium on carbon, optionally in the presence of an organic acid.

8. The process according to claim 7 wherein the hydrogenation is effected in the absence of acid.

9. The process according to claim 7 wherein the organic acid is methane sulfonic acid.

10. The process according to claim 1 wherein the moiety $AA_4$-$AA_5$-$AA_6$-$AA_7$ is cyclohexylglycine-Gln-Ser-Leu.

11. The process according to claim 1 wherein r is 3.

12. The process according to claim 1 which further comprises the additional step of reacting the dipeptide of the formula:

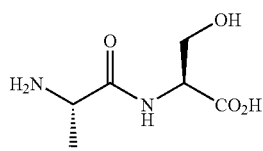

with the N-protected proline of the formula:

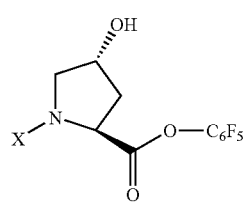

wherein X is an amino protecting group.

13. The process according to claim 1, wherein r is 3 and the moiety $AA_4$-$AA_5$-$AA_6$-$AA_7$ is cyclohexylglycine-Gln-Ser-Leu, which further comprises the step of reacting a tripeptide compound of formula C-1a:

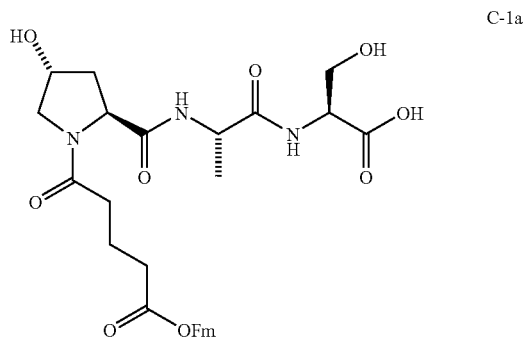

or a salt thereof;

with a tetrapeptide compound of formula F-1:

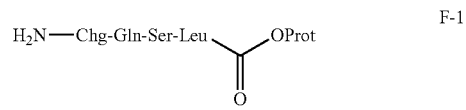

or a salt thereof.

14. The process according to claim 13 wherein the compound of the formula C1a is reacted with the compound of the formula F-1 in the presence of a carboxyl activating agent and a base.

15. The process according to claim 13 wherein the compound of the formula C1a is reacted with the compound of the formula F-1 in the presence of a carboxyl activating agent and a base and additionally in the presence of an additive.

16. The process according to claim 15 wherein the additive comprises HOAT, HOBT or 4-hydroxypyridine N-oxide.

17. The process according to claim 15 wherein the additive is 4-hydroxypyridine N-oxide.

18. The process according to claim 13 wherein Prot is benzyl.

19. The process according to claim 18 which comprises the step of treating the following compound of the formula:

(SEQ.ID.NO.: 3)

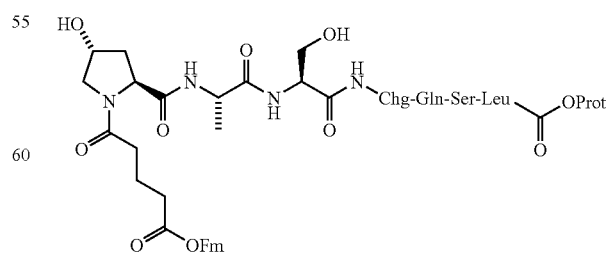

wherein Prot is benzyl, with hydrogen ($H_2$) in the presence of palladium on carbon.

20. The process according to claim 18 which comprises the step of treating the following compound of the formula:

(SEQ.ID.NO.: 3)

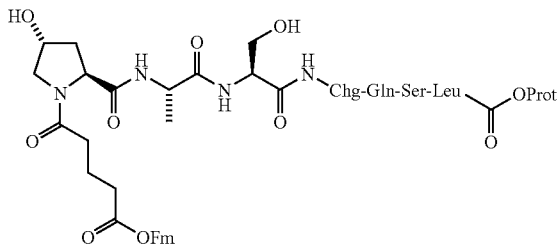

wherein Prot is benzyl, with hydrogen (H$_2$) in the presence of palladium on carbon and an organic acid.

21. The process according to claim 20, wherein the organic acid is methane sulfonic acid.

22. The process according to claim 19 which further comprises the step of purifying the crude product from the treatment with hydrogen in the presence of palladium on carbon by slurrying the crude product in a polar solvent and adding an anti-solvent.

23. The process according to claim 22 which further comprises the step of purifying the crude product from the treatment with hydrogen in the presence of palladium on carbon by slurrying the crude product in a polar solvent and adding an anti-solvent.

24. The process according to claim 22 wherein the anti-solvent comprises ethyl acetate or isopropyl acetate.

25. The process according to claim 22 wherein the anti-solvent is ethyl acetate.

26. A compound of the formula C-1a:

C-1a

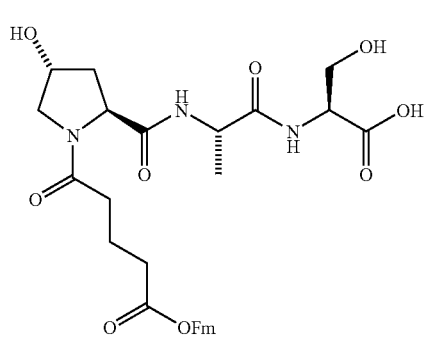

or a salt thereof.

* * * * *